United States Patent
Yaghdjian (10) Patent No.: US 9,616,158 B2
(45) Date of Patent: Apr. 11, 2017

(54) MOLDED VAD

(71) Applicant: Raffy Yaghdjian, Miami, FL (US)

(72) Inventor: Raffy Yaghdjian, Miami, FL (US)

(73) Assignee: HeartWare, Inc., Mounds View, MN (US)

( * ) Notice: Subject to any disclaimer, the term of this patent is extended or adjusted under 35 U.S.C. 154(b) by 0 days.

(21) Appl. No.: 14/560,424

(22) Filed: Dec. 4, 2014

(65) Prior Publication Data

US 2015/0151031 A1    Jun. 4, 2015

Related U.S. Application Data (60) Provisional application No. 61/911,852, filed on Dec. 4, 2013.

(51) Int. Cl.
*A61N 1/362* (2006.01)
*A61M 1/10* (2006.01)
*A61M 1/12* (2006.01)

(52) U.S. Cl.
CPC ........ *A61M 1/1012* (2014.02); *A61M 1/1031* (2014.02); *A61M 1/122* (2014.02)

(58) Field of Classification Search
USPC .......................................................... 600/16
See application file for complete search history.

(56) References Cited

U.S. PATENT DOCUMENTS

| 5,211,546 | A | 5/1993 | Isaacson et al. | |
|---|---|---|---|---|
| 6,210,133 | B1 | 4/2001 | Aboul-Hosn et al. | |
| 6,227,797 | B1 | 5/2001 | Watterson et al. | |
| 2004/0230090 | A1* | 11/2004 | Hegde | A61M 1/1053 600/18 |
| 2007/0100196 | A1* | 5/2007 | LaRose | A61M 1/101 600/16 |
| 2008/0200750 | A1 | 8/2008 | James | |
| 2012/0088954 | A1 | 4/2012 | Foster | |
| 2013/0041203 | A1* | 2/2013 | Heilman | A61M 1/10 600/16 |

OTHER PUBLICATIONS

International Search Report and Written Opinion for Application No. PCT/US2014/068581 dated Mar. 24, 2015.

* cited by examiner

*Primary Examiner* — Nicole F Johnson
(74) *Attorney, Agent, or Firm* — Christopher & Weisberg, P.A.

(57) ABSTRACT

Various blood pumps and methods of manufacture therefor are disclosed. An embodiment of a blood pump comprises a blood-flow lumen having an inlet and an outlet, and a rotor within the blood-flow lumen, the rotor having an impeller for pumping blood through the blood pump. A motor is also provided including a plurality of magnetic poles carried by the rotor, and a stator including a plurality of electrically conductive coils adjacent to and at least partially surrounding the blood-flow lumen. An over-molded monolithic enclosure covers the stator, the enclosure at least partially sealingly enclosing the stator and encasing the blood-flow lumen.

19 Claims, 12 Drawing Sheets

| ITEM NO. | QTY. | PART NUMBER | DESCRIPTION |
|---|---|---|---|
| 12 | 1 | ASY00123 | FRONT MOTOR WITH HEADER |
| 11 | 1 | DW700014 | CENTER POST, COATED |
| 10 | 1 | CMP00363 | INFLOW TUBE, OUTER, SINTERED - POLISHED |
| 9 | 1 | DW700057 | INFLOW TUBE, INNER POLISHED |
| 8 | 1 | DW400011 | CERAMIC DISK, FRONT HVAD |
| 7 | 1 | DW400007 | HOUSING, FRONT, SUPER SLIM |
| 6 | 1 | DW400018 | NUT, REAR, MOTOR CASE |
| 5 | 1 | DW400078 | INSERT RING, MOTORCASE |
| 4 | 2 | DW400022 | PIN, LOCATING |
| 3 | 1 | ASY00131 | REAR MOTOR WITH HEADER |
| 2 | 1 | DW400012 | CERAMIC DISK, REAR HVAD |
| 1 | 1 | DW400008 | HOUSING, REAR, SUPER SLIM |

FIG. 6D

MOLDED VAD

CROSS-REFERENCE TO RELATED APPLICATIONS

The present application claims the benefit of the filing date of U.S. Provisional Patent Application No. 61/911,852, filed Dec. 4, 2013, the disclosure of which is hereby incorporated herein by reference.

BACKGROUND OF THE INVENTION

Various blood pumps are known for pumping the blood of a patient to provide assistance to his/her ailing heart. Particularly, implantable, magnetically driven, rotary ventricular assist devices (VADs) are blood pumps which may, if desired, be implanted in the patient to provide assistance in pumping blood for hearts that are afflicted with congestive heart failure or the like.

Axial flow pumps for blood have the advantage of narrow width, as compared to radial flow pumps. Typically, an axial flow pump has a cylindrical housing with an inlet, an outlet, and a rotor within the housing having impeller blades attached to the rotor. A set of electrical coils is disposed around the housing to provide a rotating magnetic field which spins the rotor. As the rotor rotates, the impeller blades propel the fluid (e.g., blood) through the inlet of the pump and out of the outlet. Radial flow pumps, such as the HVAD® pump of HeartWare, Inc., the Applicant, also have applicability in pumping blood for patients afflicted with congestive heart failure or the like.

Figure 5A:
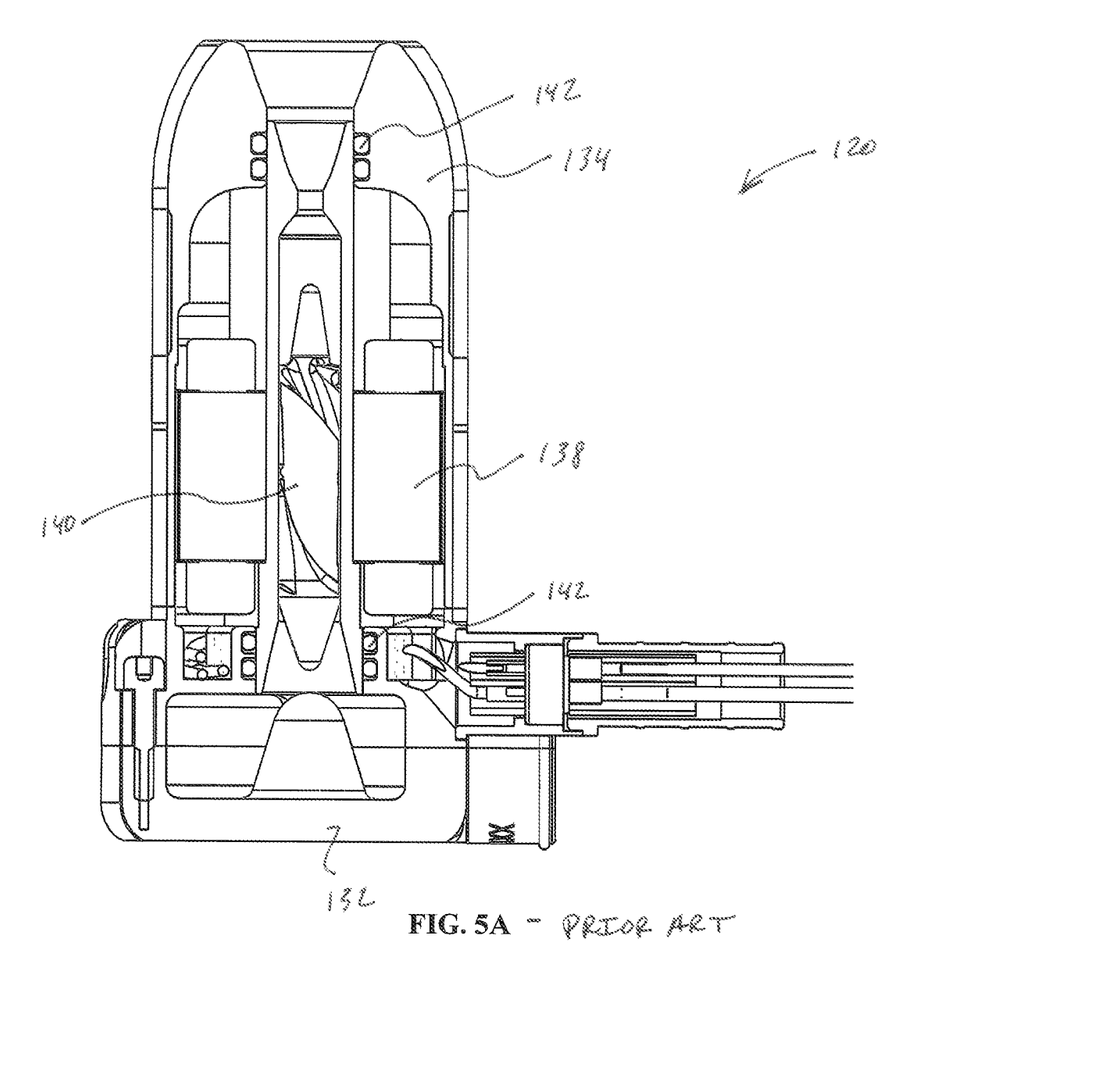
FIGS. 5A-C are cross-sectional and exploded views of a prior art blood pump of the type described above.
Figure 5B:
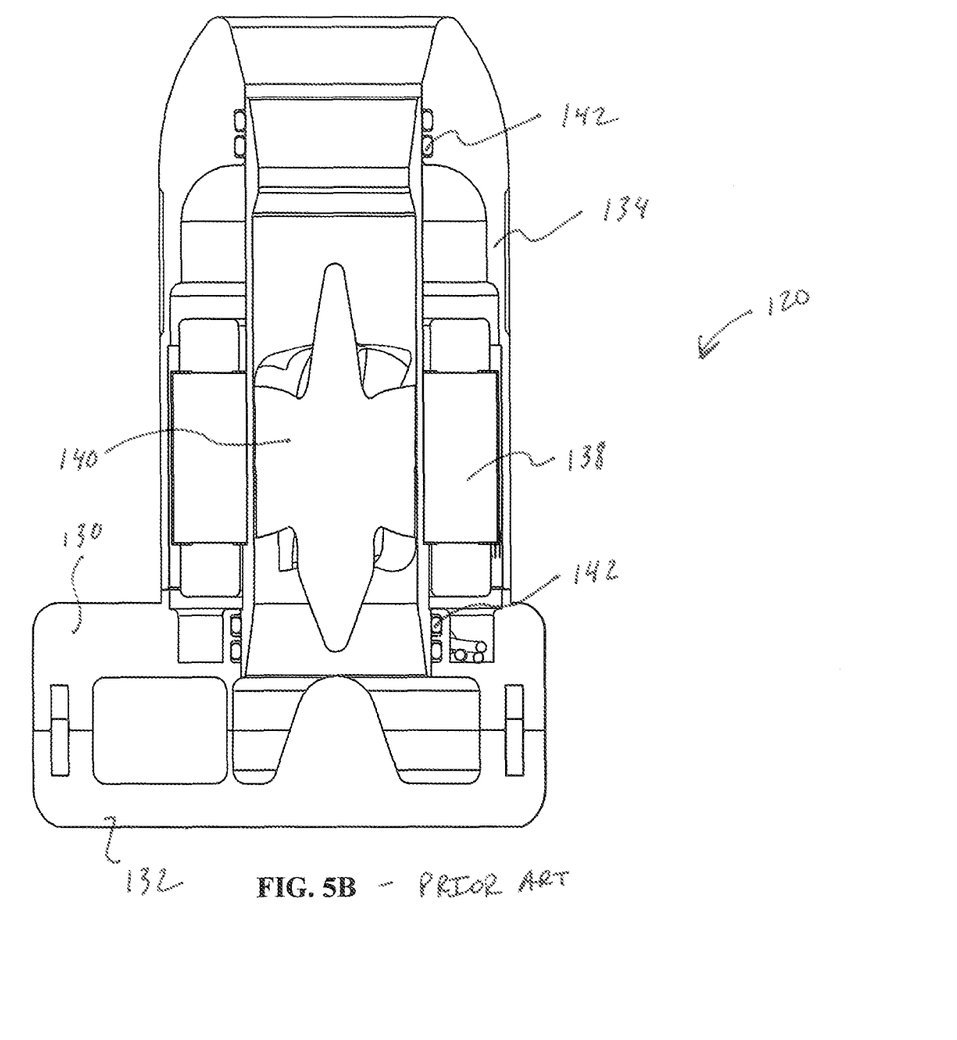
Figure 5C:
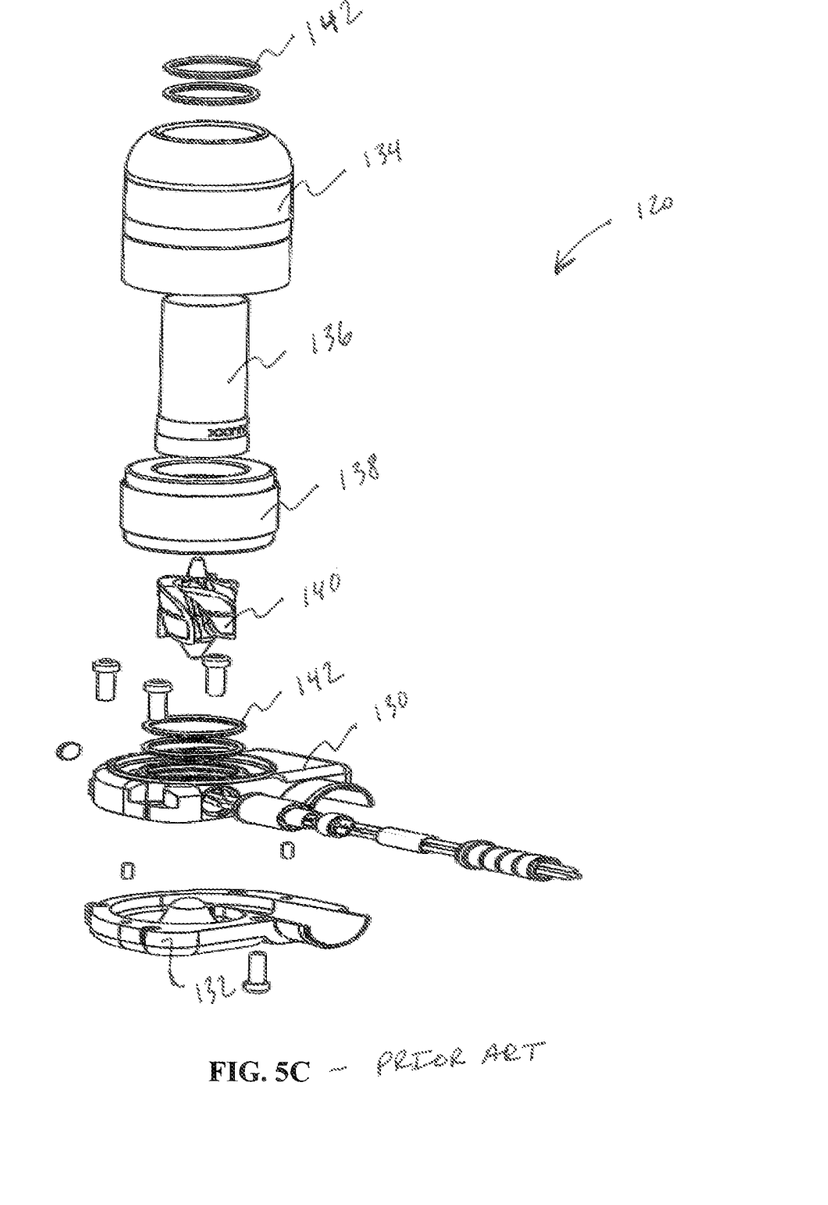

Known axial flow pumps for blood have typically been made of suitable biocompatible metals, such as titanium. Generally, the pump is not inherently sealed. Stated another way, pumps of the prior art typically include separate components that require sealing (e.g., through the use of O-rings or other sealing devices) to attempt to establish a sealed environment around the coils. An example of such a prior art pump is shown in FIGS. 5A-C. Joining of components is not always fully effective and is, in some cases, subject to failure. In addition, the multitude of components makes for a difficult and expensive assembly of the pump since there are multiple seal points to establish.

In particular reference to the pump 120 of FIGS. 5A-C, as can be seen the pump includes a variety of components that require assembly. For instance, as shown in FIG. 5C, the pump includes upper and lower volute portions 130, 132, a metal casing 134, a tubular housing 136, a stator 138, and a rotor 140. Various sealing rings 142 are also provided. In its assembled form as shown in FIGS. 5A-B, the various parts mentioned above must be pieced together and, in many cases, certain parts are adhered or connected together in some manner. For instance, stator 138 is adhered to tubular housing 136 and an epoxy backfill is used to secure stator 138 to metal casing 134 during assembly. Further, sealing rings 142 are utilized in an effort to create a sealed environment for pump 120. Assembly of pump 120 therefore requires a number of pieces and occupies time and effort to ensure pump 120 operates in a sealed environment.

BRIEF SUMMARY OF THE INVENTION

A first aspect of the present invention includes a blood pump comprising a pump housing having a chamber with an inlet and an outlet, a rotor within the chamber of the pump housing, the rotor having an impeller for pumping blood through the blood pump, a motor including a plurality of magnetic poles carried by the rotor, and a stator including a plurality of electrically conductive coils adjacent to and at least partially surrounding the pump housing. The blood pump includes an over-molded monolithic enclosure covering the stator, the enclosure and the pump housing cooperatively sealingly enclosing the stator. In some embodiments, the enclosure directly contacts the pump housing at various contact points, thereby securing the pump housing relative to the enclosure. Also, the enclosure may be composed of a biocompatible polymer.

A second aspect of the present invention includes a method of manufacturing a blood pump comprising the steps of positioning a stator within a mold, the stator including a plurality of electrically conductive coils for interacting with a rotor, and molding an enclosure around the stator while in the mold so that the enclosure at least partially sealingly encloses the stator and borders a blood-flow lumen of the pump. As with above, the enclosure may be composed of a biocompatible polymer. In embodiments of this second aspect, the stator is sealed off from the flow of blood through the blood pump by molding the enclosure around the stator in the manner described. Thus, the stator can operate freely without contact from possibly harmful fluids that might damage the stator. In an embodiment, the step of molding the enclosure includes molding the enclosure around the stator so that the enclosure forms a unitary part with the stator.

A third aspect of the present invention includes a blood pump comprising a structure having a monolithic molded enclosure, the structure defining a blood-flow lumen having an inlet and an outlet, a rotor within the blood-flow lumen, the rotor having an impeller for pumping blood through the blood pump, a motor including a plurality of magnetic poles carried by the rotor, and a stator including a plurality of electrically conductive coils adjacent to and at least partially surrounding the blood-flow lumen, wherein the molded monolithic enclosure covers the stator, the enclosure at least partially sealingly enclosing the stator and encasing the blood-flow lumen. In an embodiment, the enclosure defines the blood-flow lumen. In another embodiment, however, the structure includes a pump housing formed separately from the enclosure, the blood-flow lumen being at least partially defined by the pump housing.

BRIEF DESCRIPTION OF THE DRAWINGS

A more complete appreciation of the subject matter of the present invention and the various advantages thereof can be realized by reference to the following detailed description, in which reference is made to the accompanying drawings:

FIGS. 6A-C are various exploded, perspective, and cross-sectional views of an existing HVAD® pump, while

DETAILED DESCRIPTION

In describing certain features of the present invention, specific terminology will be used for the sake of clarity. However, the invention is not intended to be limited to any specific terms used herein.

Figure 1:
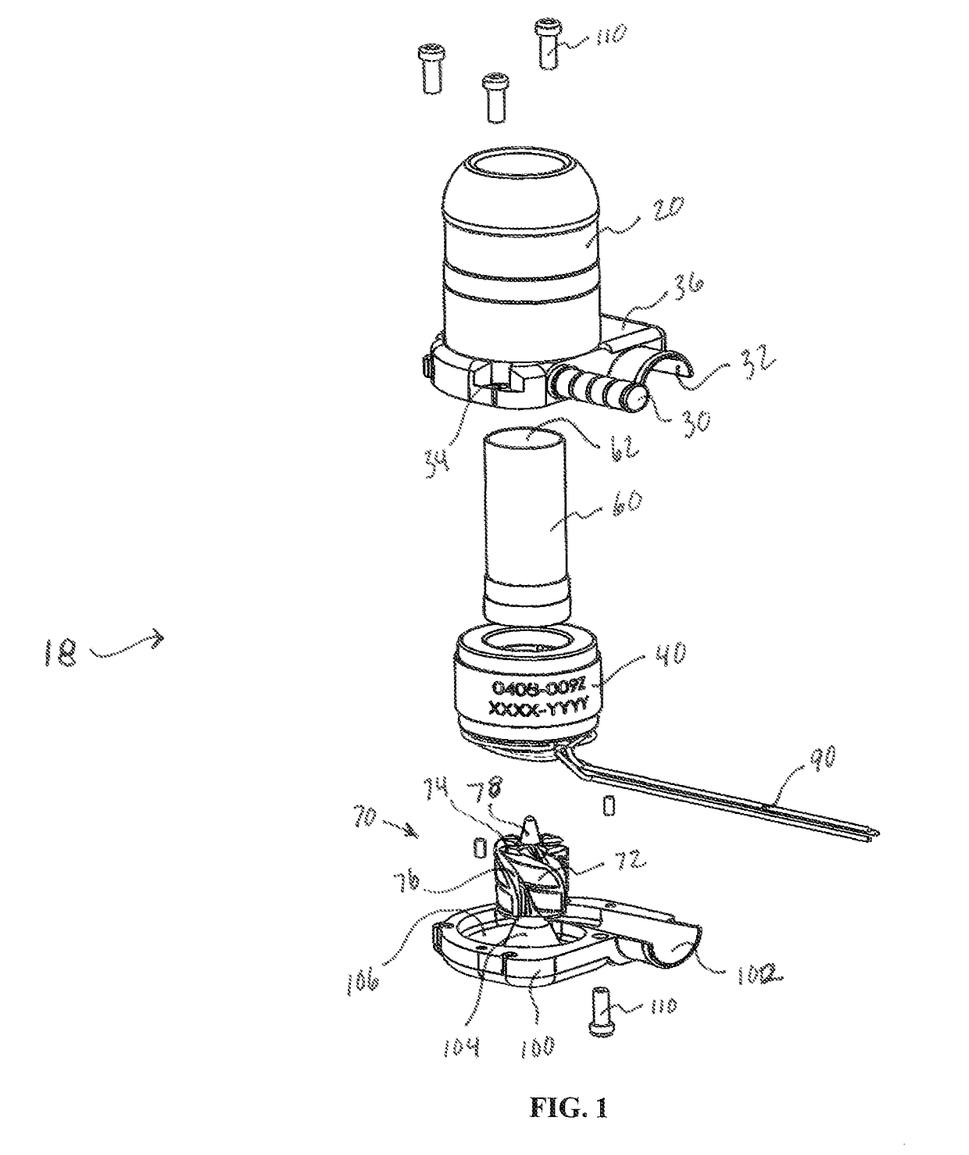
FIG. 1 is an exploded perspective view of a blood pump, according to an embodiment of the present invention.
Figure 4A:
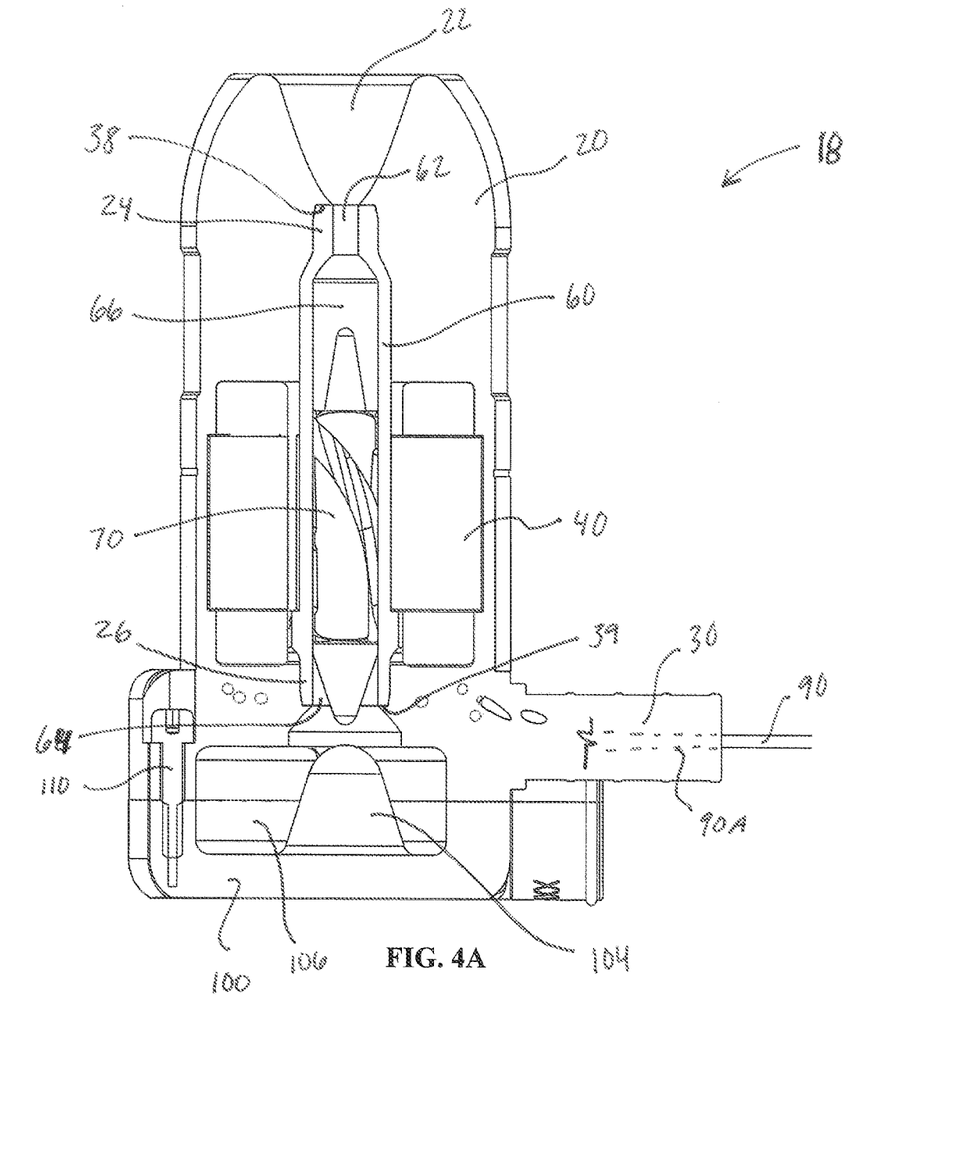
FIGS. 4A-B are cross-sectional views of the blood pump of FIG. 1, fully assembled.

FIG. 1 depicts a blood pump 18 according to an embodiment of the present invention. Blood pump 18 includes a pump housing 60. Housing 60 is a generally tubular structure formed from a non-magnetic material as, for example, a ceramic. The housing 60 has an inner chamber 66 for carrying blood or other fluid through pump 18, an inlet 62 for accepting the blood, and an outlet 64 for discharging the blood. A rotor 70 is positioned in pump housing 60 for pumping blood or other fluids through pump 18. A stator 40 (FIG. 4A) incorporating a plurality of electrical coils (not shown) surrounds pump housing 60. The coil arrangement itself may be conventional. For example, the stator may include three sets of coils. Each such set may include two coils disposed on opposite sides of the housing. The sets may be arrayed at equal spacings around the circumference of the housing. The coils are connected to an electrical cable 90, commonly referred to as a driveline, incorporating electrical leads 90A (FIG. 4A).

A monolithic enclosure 20 is, in one embodiment, formed from a biocompatible polymer that is over molded onto pump housing 60 and stator 40 to assist in creating a fully fluid-tight (in some cases hermetic) enclosure, which encompasses the exterior of pump housing 20, the stator 40, and the leads 90A of driveline 90. Blood pump 18 is therefore operable in a fluid-filled environment, such as the interior of a human or other mammalian body, to pump blood.

In one embodiment, upstream and downstream sections 24, 26 of pump housing 60 are in direct contact with enclosure to establish a seal at sections 24, 26 (e.g., a hermetic seal). For instance, enclosure 20 may be molded around pump housing 60, as described in more detail below, so that enclosure directly contacts sections 24, 26 of pump housing 60 to establish an immediate seal with pump housing 60 at sections 24, 26. Pump housing 60 also includes an inner chamber 66 for carrying blood or other fluid through pump 18, an inlet 62 for accepting the blood, and an outlet 64 for discharging the blood. In addition, since enclosure 20 contacts pump housing 60 (e.g., at upstream and downstream sections 24, 26), it is stabilized in the upstream-to-downstream direction relative to enclosure 20.

As shown in FIGS. 3A-B and 4A-B, enclosure 20 defines an inlet 22. An upper lip 38 may be formed on enclosure 20 for overlying an upstream edge of pump housing 60 (e.g., the edge of its inlet 62) so that a seamless transition is provided between inlet 22 of enclosure 20 and inlet 62 of pump housing 60. Likewise, a lower lip 39 may be formed on enclosure 20 for overlying a downstream edge of pump housing 60 (e.g., the edge of its outlet 64) so that a seamless transition is provided between outlet 64 of pump housing 60 and a downstream portion of enclosure 20. In one embodiment, inlet 62 of pump housing 60 is also reduced in diameter as compared to its outlet 64, as shown. Although enclosure 20 may be formed with upper and lower lips 38, 39 providing seamless transitions, it is also contemplated that pump housing 60 may provide the sole inlet to pump 18 and enclosure 20 may, for example, be molded about a middle section of pump housing 60. Thus, in this embodiment, the ends of pump housing 60 may protrude somewhat from the ends of enclosure 20.

As shown in FIGS. 3A-4B, an annular cavity 28 is formed between pump housing 60 and enclosure 20 for housing stator 40. Cavity 28 circumferentially surrounds pump housing 60 and receives stator 40. In one embodiment, enclosure 20 is molded around pump housing 60 (e.g., injection molded) while stator 40 is positioned on housing 60 so that molded enclosure 20 contacts stator 40 and precisely forms cavity 28 to conform to the shape of stator 40. In this manner, stator 40 is secured relative to enclosure 20 and pump housing 60 by virtue of over molding. Stated another way, when enclosure 20 is molded around pump housing 60 and stator 40, it forms a unitary part with pump housing 60 and stator 40 and secures such components relative to each other. The enclosure also encompasses leads 90A of drive line 90. The enclosure defines a driveline conduit 30 projecting away from the housing. The driveline 90 extends out of the enclosure through conduit 30. Desirably, conduit 30 is formed in the same molding operation used to form the remainder of enclosure 20. Thus, the material of the enclosure bonds to the exterior of the driveline and forms a seal. Thus, without additional seals or other components, stator 40 and its cavity 28 are effectively sealed from chamber 66 of pump housing 60 and the flow of blood therethrough. A long-lasting fully-sealed environment is therefore established in which pump 18 can operate without the worry of leaking or failure of the sealed environment. Fewer components are also used to establish the sealed environment. As mentioned above, in one embodiment the environment is hermetic. In addition, enclosure 20 may be molded over pump housing 60 and stator 40 so that enclosure 20 contacts other points besides upstream and downstream sections 24, 26, and establishes a seal at those points.

Figure 3A:
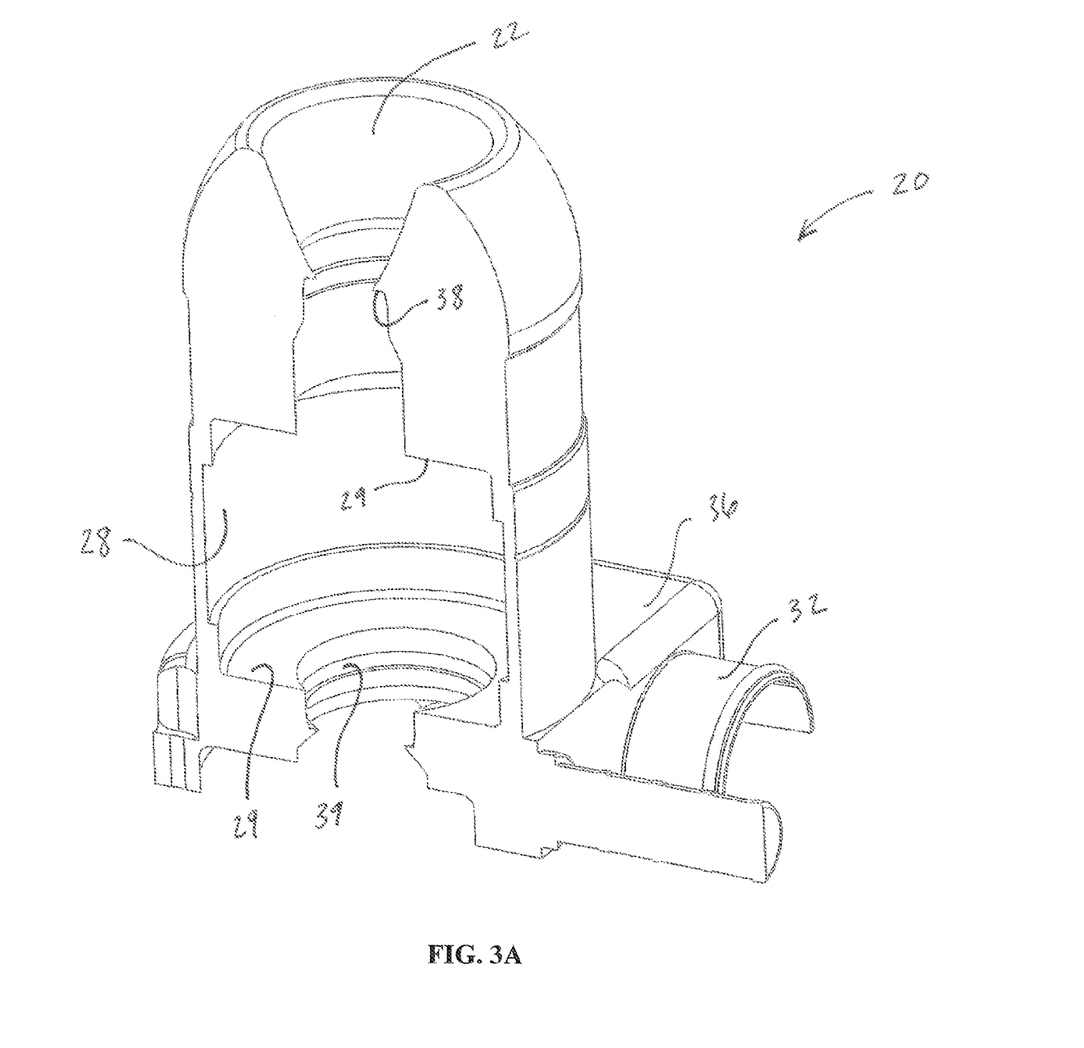
FIGS. 3A-B are cross-sectional views of the top part of FIG. 2.
Figure 3B:
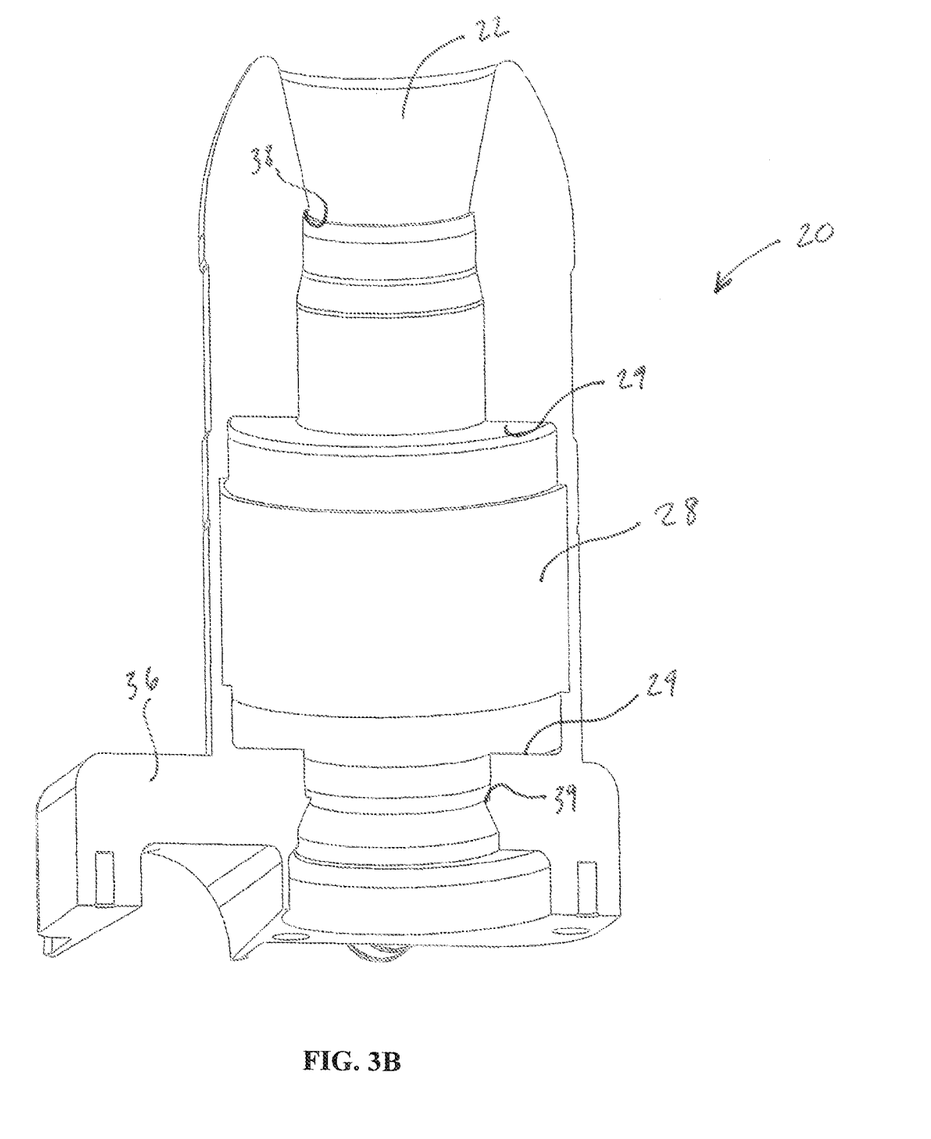
Figure 4B:
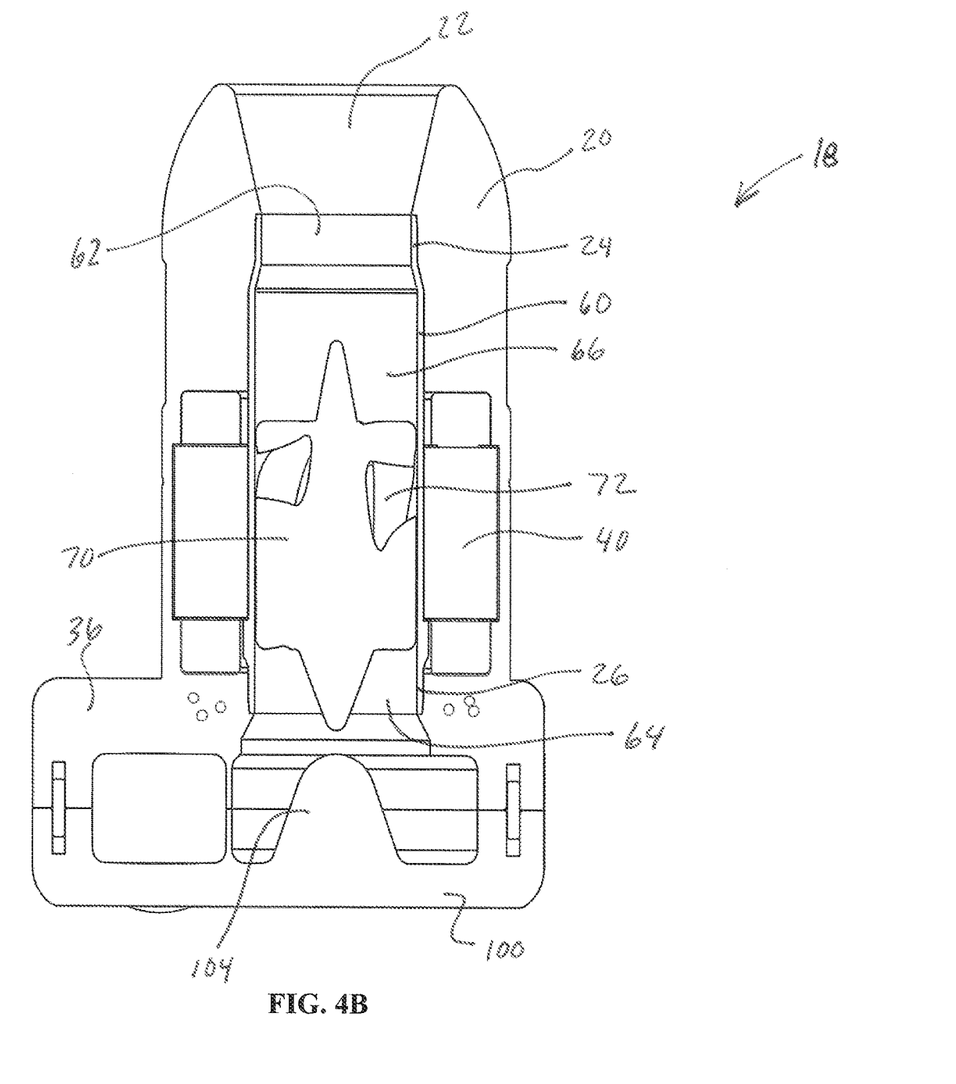

In a particular embodiment, enclosure 20 is molded over stator 40 in such a way as to form a cavity 28 with surfaces 29 transverse to an upstream-to-downstream direction (FIGS. 3A-B). Surfaces 29 abut the ends of stator 40, as shown in FIGS. 4A-B, so that stator 40 is secured in the upstream-to-downstream direction. In other words, surfaces 29 are separated by a distance that is approximately equal to or only insignificantly greater than a distance between the ends of stator 40 so that stator 40 is secured in the upstream-to-downstream direction. Because of this, stator 40 does not need to be secured to pump housing 60, as is the case in certain prior art pumps. For example, certain prior art pumps include a pump housing that is adhered to the stator (e.g., through adhesion/cure techniques) to further secure it in position. This is the case with pump 120 of FIGS. 5A-C. With blood pump 18, no such step is needed. Instead, stator 40 is secured in the upstream-to-downstream direction relative to pump housing 60 by way of molding enclosure 20 over stator 40 and housing 60. Cavity 28 is likewise formed to facilitate securing stator 40 relative to pump housing 60 and to conform to the shape of stator 40. Thus, stator 40 remains in position relative to pump housing 60 during operation so that rotor 70 can be appropriately positioned, and remain in position, in chamber 66 of pump housing 60.

As shown in FIGS. 1 and 4A-B, drive line wires 90 may be connected to stator 40 to control the operation thereof, either prior to or after the molding process for enclosure 20. Wires 90 may be connected to terminals on stator 40, for example three (3) terminals for three-phase operation of stator 40, and wrapped around stator 40 exiting through cable conduit 30 of enclosure 20. Wires 90 may also be wrapped about a section of pump housing 60 for strain relief purposes. Drive line 90 extends from stator 40 to a controller (not shown), which provides power for operating stator 40 and blood pump 18. The controller may be outside of the patient's body, or may be an internal implantable controller. If an internal controller is used, it may be associated with a battery having inductive charging capabilities for charging the battery for pump 18.

Figure 2:
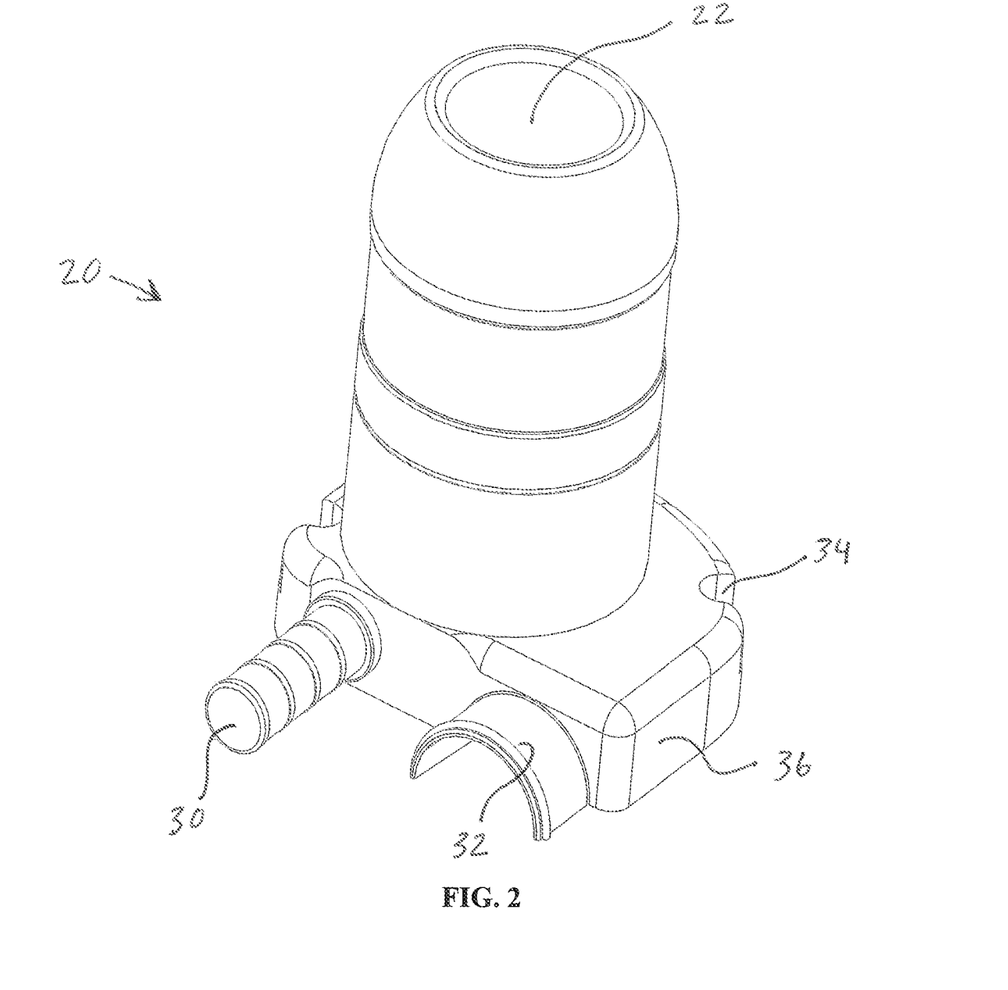
FIG. 2 is a perspective view of a top part of the blood pump of FIG. 1.

Referring now to FIGS. 1-2, enclosure 20 is also molded so as to have an upper volute portion 36 defining part of an outlet of pump 18. In particular, as shown in FIGS. 3A-B, upper volute portion 36 is unitary with the rest of enclosure 20, it being a unitary molded part, and includes a disc-like chamber that is arranged to accept blood or other fluid from outlet 64 of pump housing 60. Upper volute portion 36 also includes outlet portion 32, which is roughly semi-tubular in shape.

One or more openings 34 is provided in enclosure 20 adjacent upper volute portion 36 so as to connect upper volute portion 36 with a lower volute portion 100, as shown in FIGS. 1 and 4A. In particular, one or more rivets, screws, or other fixation mechanisms 110 are inserted through opening(s) 34 to secure upper volute portion 36 to a lower volute portion 100 and form a complete volute having an outlet. Referring to FIGS. 1 and 4A-B, lower volute portion 100 includes an annular chamber 106 defined by a center post 104 (in some cases domed), and an outlet portion 102 for interacting with outlet portion 32 of upper volute portion 36. Once lower volute portion 100 is connected to upper volute portion 32 via fixation mechanism(s) 110, as shown in FIGS. 4A-B, a complete volute with an outlet for discharging blood is formed. Blood can therefore travel through pump 18, in particular chamber 66 of pump housing 60, and exit into the volute to be driven into circumferential flow by center post 104 and subsequently out of the outlet defined by outlet portions 32, 102. In other words, counter pressure generated by rotor 70 may cause blood or other fluid to interact with center post 104 and move circumferentially within the volute and out of its outlet.

Rotor 70 may be any suitable rotor for fitting within chamber 66 of pump housing 60 and driving blood through pump 18. In one embodiment, rotor 70 includes an impeller defining various blades 74 used to impel blood through pump 18. The blades may have spaces or channels 76 between them for channeling blood through rotor 70. In addition, one or more hydrodynamic surfaces 72 may be included on rotor 70 for creating a frictionless operation within pump 18. Stated another way, hydrodynamic surfaces 72 may be included with rotor 70 so that a layer of blood forms a barrier between rotor 70 and pump housing 60 and rotor 70 can rotate within pump housing 60 against the layer of blood in a frictionless or near-frictionless environment. Hydrodynamic surfaces 72 may also act to cause rotation of rotor 70. Hydrodynamic surfaces of the type disclosed herein are described in detail in U.S. Pat. No. 8,007,254, assigned to the Applicant, HeartWare, Inc., the disclosure of which is incorporated by reference herein. Any of the rotors of the '254 patent may be utilized with blood pump 18, if desired. Likewise, any of the disclosed stators of the '254 patent could be utilized with blood pump 18 as well.

Rotor 70 may be composed of a magnetic alloy, such as platinum cobalt, and may include a plurality of permanent drive magnets for interacting with stator 40. Again, such drive magnets are described in the '254 patent. Rotor 70 is hydrodynamically and/or magnetically suspended in pump housing 60 by virtue of its interaction with stator 40, and is operable to rotate within chamber 66 once stator 40 is activator to drive blood through pump 18. As stator 40 is secured relative to pump housing 60 in the manner described above (e.g., through molding), rotor 70 is also stabilized within chamber 66 during operation. In other words, since stator 40 is secure in the upstream-to-downstream direction, the position of rotor 70 will not be affected by any unintended movement of stator 40.

In use, blood pump 18 is implanted within a patient suffering from, for example, congestive heart failure to assist in pumping of blood from the heart. Blood pump 18 may be positioned to support either a left ventricle of the heart (LVAD) or a right ventricle (RVAD). In some cases, blood pump 18 is implanted into the pericardial space directly adjacent to the heart (e.g., with inlet 22 in either the right or left ventricle at the respective apex). The outlet defined by outlet portions 32, 102 is positioned outside of the heart and is attached to a tubular conduit (not shown), referred to as a graft. Where the inlet is positioned in a ventricle, the graft is in turn connected to the aorta to establish blood flow through pump 18 and to the aorta. In some cases, a sewing ring is utilized to mount pump 18 on the heart, and an apical coring tool is used to establish access to the heart.

The molding process for pump 18 uses an appropriate biocompatible material, for instance a thermoplastic such as polyether ether ketone (PEEK), a PEEK composite, or any other suitable implantable grade polymer, optionally having one or more of the following properties: rigid, good electrical insulation properties, chemical resistance, and able to withstand sterilization processes (e.g., ETO). While the use of an injection-molding system is described below, it is recognized that any suitable molding system may be used (e.g., transfer molding), and that the description of injection molding herein is only exemplary. In a particular embodiment, after selecting the appropriate material, an injection mold (not shown) shaped to produce the desired exterior shape of enclosure 20 is provided. Pump housing 60 with a stator 40 surrounding it is then inserted into the mold. The mold may have a highly-polished surface finish so as to achieve a smooth exterior surface for pump 18 via the molding process. Proper equipment is used to stabilize pump housing 60 and stator 40 within mold so that such components are not mistakenly moved during the injection molding process. In one embodiment, drive line 90 is also connected to stator 40 while in the mold, and leads 90A extend out of the mold by some distance so that the entirety of line 90 is not over molded (e.g., to allow for later connection to other components). An alternate embodiment allows for drive line 90 to be connected after the molding process.

A shot of the biocompatible material is then heated and forced under pressure into the mold where it surrounds pump housing 60, stator 40, and drive line 90 to form enclosure 20. A unitary part is therefore established comprising pump housing 60, stator 40, and enclosure 20. As described previously, during the molding process enclosure 20 directly contacts and bonds to upstream and downstream sections 24, 26 of pump housing 60, effectively establishing a seal (e.g., hermetic) at those sections 24, 26 to seal off stator 40 (and its cavity 28) from the rest of pump 18. The unitary part comprising pump housing 60, stator 40, and enclosure 20 can then be attached with the other components of pump 18 (e.g., lower volute 100, rotor 70, a controller, etc.) for implantation and use within the patient.

Although the foregoing embodiments are described as utilizing certain structures, others may also be employed and are equally contemplated within the scope of the invention. For example, although a separately-formed pump housing 60 is utilized with blood pump 18, it is not a necessary component and may be omitted, in one embodiment. In this case, stator 40 may be positioned in a mold and a biocompatible material of the type discussed above (or another material) may be molded over stator so as to establish an enclosure 20 that has a continuous lumen through it from an inlet side 22 to an outlet. Thus, instead of supplying pump housing 60 and enclosure 20 to establish a blood-flow lumen, it is contemplated that enclosure itself may be molded over stator 40 in such a way to establish a blood-flow lumen without pump housing 60. Stated another way, in this embodiment the material of the enclosure also forms the pump housing, and the pump housing is part of the same monolithic element as the enclosure. In certain embodiments, the flow lumen of such an enclosure 20 may also be surface treated or hardened to provide for improved characteristics in the flow-lumen area. Thus, in this embodiment, stator 40 is sealed from the blood-flow lumen (e.g., hermetically), but enclosure 20 itself defines the lumen via the molding process.

As another option, while rotor 70 is disclosed as being composed of platinum cobalt, it may alternatively be injection molded (or ceramic injection molded—CIM) out of a biocompatible material. In this instance, a series of permanent magnets may be molded into rotor 70 (e.g., on surfaces of the impeller blades) so that rotor 70 can interact properly with stator 40 and rotate to drive blood through blood pump 18. In another example, the molded rotor may have a slot(s) in the blades to allow the insertion of a permanent magnet(s) after molding.

In a variant of the process discussed above, the enclosure may be formed from a thermosetting polymeric material such as an epoxy, which cures by chemical reaction in the mold.

In yet another variant, lower volute 100 may be composed of a metal material (e.g., titanium), any of the biocompatible polymer materials discussed above, or a combination thereof. Indeed, lower volute 100 (or a portion thereof, for instance its center post 104) is composed of titanium or another suitable metal in one embodiment to improve the durability of lower volute 100 (and/or the portion made of metal). In particular, center post 104 may be composed of titanium or another suitable metal to increase its durability while the reminder of lower volute 100 may be composed of any of the biocompatible polymer materials noted above. In such an embodiment, center post 104 may be insert molded with the remainder of polymer lower volute 100. Alternatively, the entirety of lower volute 100 may be metal.

Figure 6A:
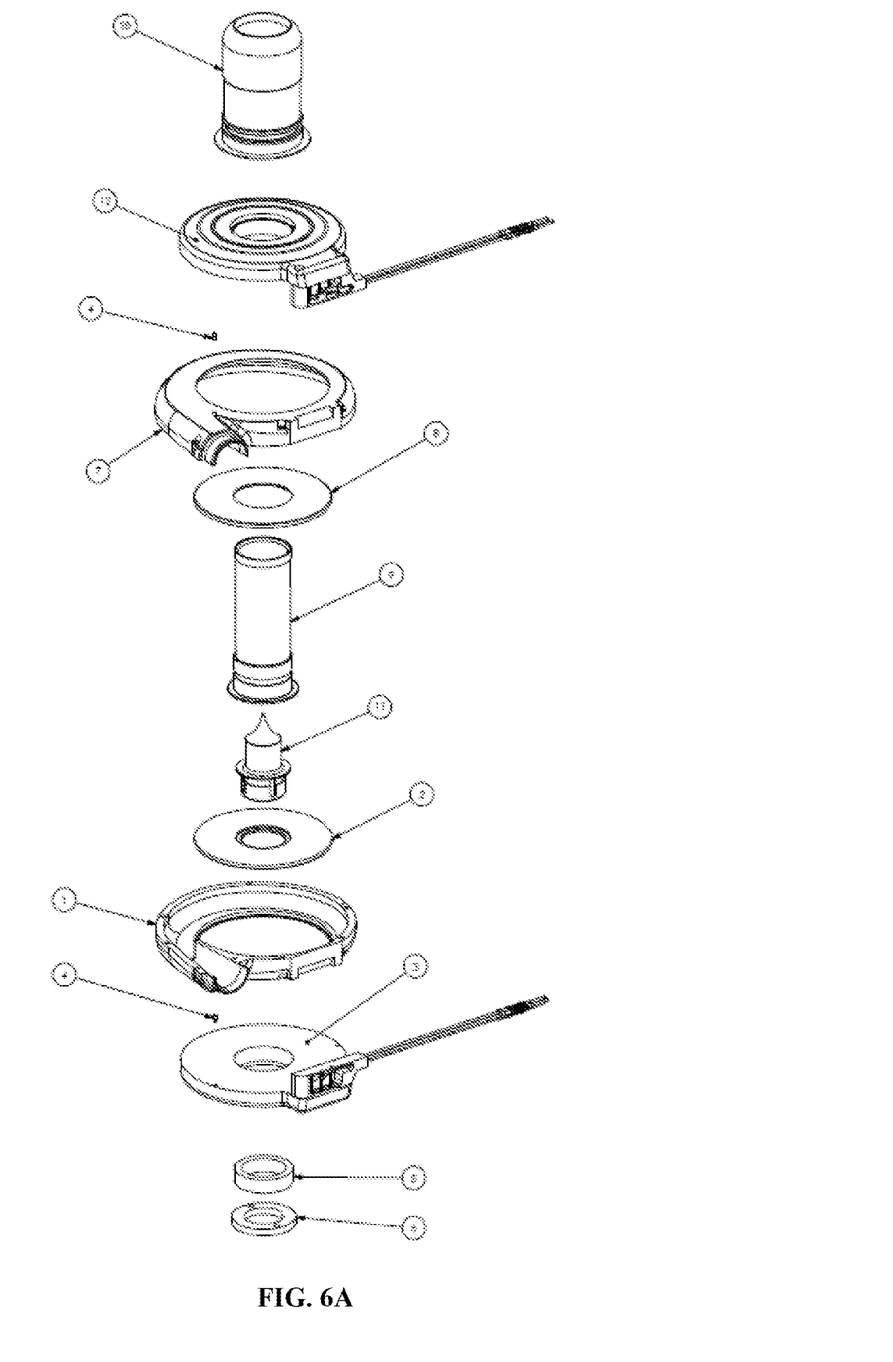
Figure 6B:
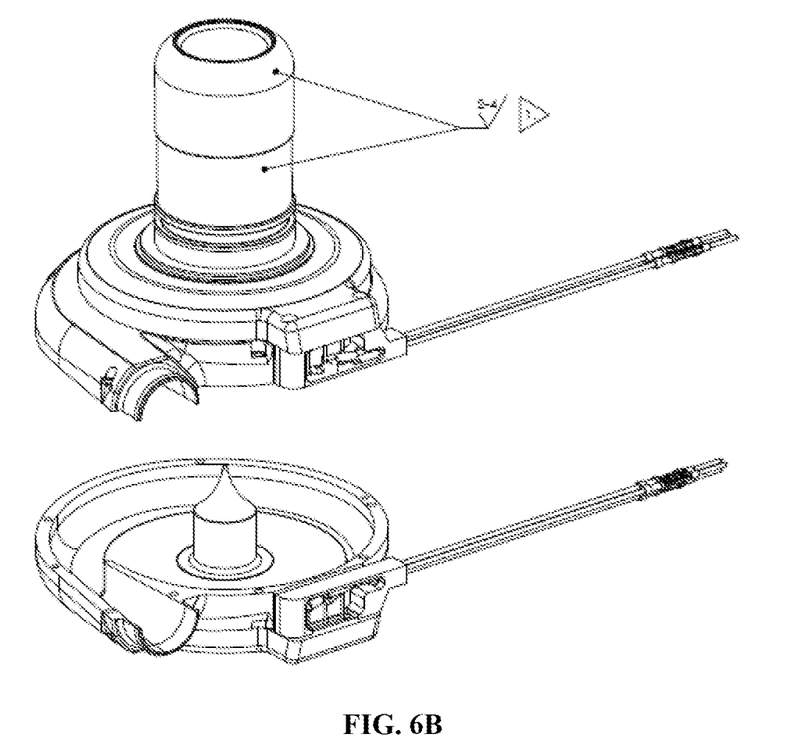
Figure 6C:
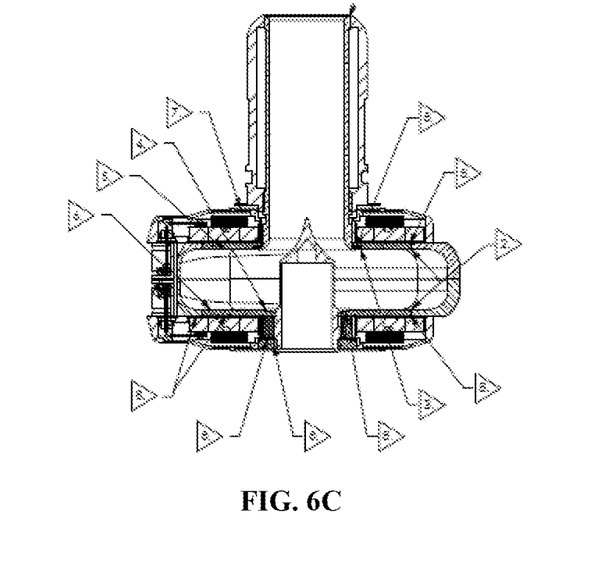
Figure 6D:
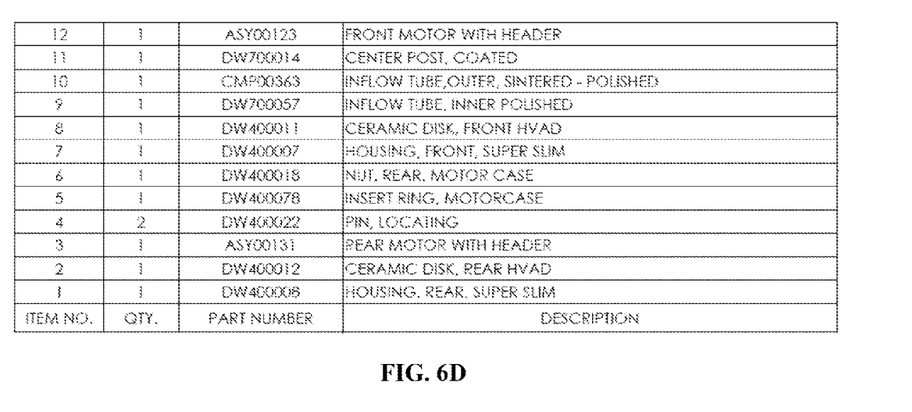
FIG. 6D is a chart detailing the components thereof.

Further, while the above-described molding process is disclosed as being usable with an axial flow pump, it is equally usable with a radial flow pump having, for example, a centrifugal pump. Such a pump is offered by the Applicant, HeartWare, Inc., as its HVAD® pump. An existing HVAD® pump of the type described is shown in detail in FIGS. 6A-C, with the components thereof designated in the chart shown in FIG. 6D. In one embodiment, it is contemplated that parts 10, 12, 4, 7, 8, and 9 may be molded as a first unitary piece using any of the aforementioned molding processes, and that parts 2, 1, 4, 3, 5, and 6 may be molded as a second unitary/composite piece. Further, the first and second unitary pieces may then be joined together to form the HVAD® device. In addition, although not shown, a centrifugal impeller of the type used in the HVAD® pump may be fitted around center post 11 to pump blood within the cavity created by the first and second unitary pieces (FIG. 6C). The centrifugal impeller is operated by front and rear motors 12, 3. In these embodiments, the molding of the first and second unitary pieces can sealingly enclose front and rear motors 12, 3 (e.g., without additional parts and/or seals) so that such are isolated from the flow of blood through the HVAD® pump. Other molded combinations beyond that discussed above are also contemplated, of course.

In yet another variant, a sensor may be embedded into a portion of enclosure 20 of pump 18 during the molding process. For instance, a sensor capable of taking diagnostic measurements concerning the operation of pump 18 and/or the patient may be embedded into enclosure 20. In one embodiment, an accelerometer may be embedded in enclosure 20 for determining the positioning of pump 18. The sensor may be connected to an electrical lead, fiber optic cable, or other suitable connection for conveying the information gleaned via the sensor to the pump 18's controller, or to an external system. The sensor alternatively could have wireless capabilities for transmitting such information. Thus, the sensor could allow for ascertaining significant information concerning pump 18's operation, its position, or the condition of the patient.

While the pump of this invention is also described in terms of a blood pump, it is contemplated that the pump might be used for pumping other fluids as well.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will also be appreciated that the various dependent claims and the features set forth therein can be combined in different ways than presented in the initial claims, and that the features described in connection with individual embodiments may be shared with others of the described embodiments. In particular, as understood by one of skill in the art, the features of any dependent claim may be shared with a separate independent or dependent claim, to the extent feasible.

The invention claimed is:

1. A blood pump comprising:
    a pump housing having a chamber defining a blood-flow lumen with an inlet and an outlet;
    a rotor within the blood-flow lumen of the chamber of the pump housing, the rotor having an impeller for pumping blood through the blood-flow lumen of the blood pump;
    a motor including a plurality of magnetic poles carried by the rotor, and a stator including a plurality of electrically conductive coils adjacent to and at least partially surrounding the blood-flow lumen of the pump housing;
    an over-molded monolithic enclosure covering the stator and encasing the blood-flow lumen, the enclosure and the pump housing cooperatively sealingly enclosing the stator.

2. A blood pump as claimed in claim 1, wherein the enclosure directly contacts surfaces of the stator, thereby securing the stator relative to the enclosure.

3. A blood pump as claimed in claim 1, wherein the enclosure includes an inlet passage fluidly connected with the inlet of the pump housing.

4. A blood pump as claimed in claim 1, wherein the pump housing is formed separately from the enclosure.

5. A blood pump as claimed in claim 1, wherein the pump housing and the enclosure are formed together monolithically.

6. A blood pump as claimed in claim 1, wherein the pump housing has an axis and end surfaces transverse to the axis, the end surfaces being separated by a first distance in the direction of the axis, and wherein the enclosure defines a pump housing chamber with end surfaces transverse to the axis that abut the end surfaces of the pump housing.

7. A blood pump as claimed in claim 1, wherein the enclosure directly contacts the pump housing at various contact points, thereby securing the pump housing relative to the enclosure.

8. A blood pump as claimed in claim 7, wherein a seal is established between the pump housing and the enclosure at the contact points, thereby sealingly enclosing the stator.

9. A blood pump as claimed in claim 1, wherein the enclosure is composed of a biocompatible polymer.

10. A blood pump as claimed in claim 1, wherein the monolithic enclosure includes an upper volute portion and the outlet of the chamber communicates with the upper volute portion, and wherein the pump further comprises a lower volute portion engageable with the upper volute portion to form a volute.

11. A blood pump as claimed in claim 1, wherein the monolithic enclosure encapsulates portions of leads connected to the stator and operative to control the stator, the leads being wrapped around a portion of the pump housing.

12. A blood pump as claimed in claim 1, wherein a sensor is embedded in a portion of the pump.

13. A blood pump as claimed in claim 4, wherein the monolithic enclosure forms a unitary part with the pump housing and the stator.

14. A blood pump comprising:
   a structure having a monolithic molded enclosure, the structure defining a blood-flow lumen having an inlet and an outlet;
   a rotor within the blood-flow lumen, the rotor having an impeller for pumping blood through the blood pump;
   a motor including a plurality of magnetic poles carried by the rotor, and a stator including a plurality of electrically conductive coils adjacent to and at least partially surrounding the blood-flow lumen,
   wherein the molded monolithic enclosure covers the stator, the enclosure at least partially sealingly enclosing the stator and encasing the blood-flow lumen.

15. A blood pump as claimed in claim 14, wherein the enclosure defines the blood-flow lumen.

16. A blood pump as claimed in claim 14, wherein the structure includes a pump housing formed separately from the enclosure, the blood-flow lumen being at least partially defined by the pump housing.

17. A blood pump as claimed in claim 16, wherein the enclosure directly contacts the pump housing at various contact points, thereby securing the pump housing relative to the enclosure, and a seal is established between the pump housing and the enclosure at the contact points.

18. A blood pump as claimed in claim 16, wherein the pump housing is tubular, and the enclosure contacts upstream and downstream portions of the pump housing, but not a middle portion of the pump housing.

19. A blood pump as claimed in claim 18, wherein an inner surface of the enclosure is spaced apart from the middle portion of the pump housing to define a stator chamber sized to receive the stator.

* * * * *

UNITED STATES PATENT AND TRADEMARK OFFICE
CERTIFICATE OF CORRECTION

PATENT NO.         : 9,616,158 B2
APPLICATION NO.    : 14/560424
DATED              : April 11, 2017
INVENTOR(S)        : Raffy Yaghdjian Page 1 of 1

It is certified that error appears in the above-identified patent and that said Letters Patent is hereby corrected as shown below:

In the Claims

Column 8, Claim 1 Line 47, insert the following -- wherein the pump housing has an axis and end surfaces transverse to the axis, the end surfaces being separated by a first distance in the direction of the axis, and wherein the enclosure defines a pump housing chamber with end surfaces transverse to the axis that abut the end surfaces of the pump housing. --

Signed and Sealed this
First Day of August, 2017

Joseph Matal
*Performing the Functions and Duties of the*
*Under Secretary of Commerce for Intellectual Property and*
*Director of the United States Patent and Trademark Office*